United States Patent [19]

Kocache et al.

[11] 4,238,308
[45] Dec. 9, 1980

[54] DEVICE FOR MONITORING A COMPONENT IN A FLUID MIXTURE

[75] Inventors: Riad M. A. Kocache; Danny F. Holman; Ronald H. Sunderland, all of Crowborough, England

[73] Assignee: Sybron Corporation, Rochester, N.Y.

[21] Appl. No.: 945,416

[22] Filed: Sep. 25, 1978

[30] Foreign Application Priority Data

Sep. 30, 1977 [GB] United Kingdom ............... 40817/77

[51] Int. Cl.³ .............................................. G01N 27/58
[52] U.S. Cl. ................................................ 204/195 S
[58] Field of Search ............... 204/1 S, 195 S; 324/29; 422/98

[56] References Cited

U.S. PATENT DOCUMENTS

| 3,546,086 | 12/1970 | Sayles | 204/195 S |
|---|---|---|---|
| 3,691,023 | 9/1972 | Ruka et al. | 204/195 S |
| 3,720,594 | 3/1973 | Wilson | 204/195 S |
| 3,723,279 | 3/1973 | Fruehan et al. | 204/195 S |
| 3,738,341 | 6/1973 | Loos | 204/195 S |
| 3,865,707 | 2/1975 | Sayles | 204/195 S |
| 3,928,161 | 12/1975 | McIntyre et al. | 204/195 S |
| 3,962,866 | 6/1976 | Neidhard et al. | 204/195 S |
| 3,977,830 | 8/1976 | Topol | 204/195 S |
| 4,040,930 | 8/1977 | Dillon | 204/195 S |
| 4,057,477 | 11/1977 | Weyl et al. | 204/195 S |
| 4,088,543 | 5/1978 | Ruka | 204/195 S |

FOREIGN PATENT DOCUMENTS

| 2272395 | 12/1975 | France | 204/195 S |
|---|---|---|---|
| 48083 | 5/1966 | German Democratic Rep. . | |
| 61367 | 4/1968 | German Democratic Rep. . | |

Primary Examiner—G. L. Kaplan
Attorney, Agent, or Firm—Theodore B. Roessel; Joseph C. MacKenzie

[57] ABSTRACT

An oxygen sensor having a solid electrolyte tube and partition. A heater is tightly wound along the length of the tube, which is divided into two equal chambers by the partition, and thermocouples are fixed to either side of the partition by layers of metallic particles. An insulating case and flame trap may be provided for the sensor.

6 Claims, 12 Drawing Figures

DEVICE FOR MONITORING A COMPONENT IN A FLUID MIXTURE

The present invention relates to a device for monitoring a component in a fluid mixture and more particularly to such a device which utilizes a solid electrolyte.

Work on the properties of solid electrolytes has been going on in many countries since the last century. Haber and St. Tolloczko were the first to study quantitatively the chemical changes of solid electrolytes and to find that they obeyed Faraday's law. Haber and others built high temperature concentration cells using solid electrolytes which measured the e.m.f. produced by reactions between gases such as Co and $O_2$ on one side of the cell keeping a constant $O_2$ concentration on the other side. This enabled the calculation of thermodynamic data for the gas at different temperatures. It was proposed to use this method for power generation, fuel cells, and for gasanalysis.

The validity of the Nernst equation:

$$e.m.f. = RT/NF \ln C_2/C_1 \qquad (1)$$

where:
R—Universal gas constant
T—Absolute temperature
F—Faraday constant
N—Number of electrons transferred
$C_1$—Concentration of a component on one side of electrolyte.
$C_2$—Concentration of same component on the other side of electrolyte.

(The e.m.f. is proportional to the chemical potential of the component under equilibrium conditions which in turn is related to its concentration or its partial pressure in gases).
was first demonstrated for solid electrolytes by Katayama who used amalgam concentration cells of the form By choosing an electrolyte system with the following features:
(i) does not form deposits on the electrodes,
(ii) has the same basic reaction on either electrode,
(iii) has nearly pure ionic conductivity, and
(iv) has a conducting ion which is of interest,
cells of the types mentioned can be utilized in a variety of modes:
(a) as concentration cells—if the concentration of a component on one side is known (reference) the output e.m.f. will be related to the concentration of that component on the other side, concentration meter, thermodynamic data, etc.
(b) As fuel cells for electric power generation, and
(c) as pumps—if an electronic current is passed through the electrolyte with the appropriate component having concentration $C_1$ and $C_2$ on either side a transfer of part of the component from one side to the other is effected, the extent of which is primarily determined by the amount of electric current passed.
For each of these modes, the cell design, the electrolyte material, and the electrode material is a matter of consideration.

Extensive use was made of solid electrolytes in the construction of galvanic cells to gather thermodynamic data and in the construction of fuel cells. Disc shaped solid electrolytes made of solid solutions such as CaO in $ZrO_2$ and having oxygen ion vacancies in cells of the type A, A(O)/solid electrolyte/B,B(O) where, A(O)—metal oxide of metal A,
B(O)—metal oxide of metal B, have been used to determine the molar free energy of formation for a variety of oxides, sulfides and tellurides at elevated temperatures. Their work re-generated interesting the use of mixed crystals as solid electrolytes.

Now Nernst had observed, at the turn of the century, the evolution of oxygen at the anode whilst passing a D.C. current in his "glow bar" element, which he usually made of mixed crystal solid solutions such as 0.85 $ZrO_2$ 0.15 $Y_2O_3$. Wagner and Schotky related, thermo dynamically, the ionic defect concentrations of a compound (ionic or solid solution), and the deviation of the composition from exact stoichiometry, to the activity of the component in the surroundings. Wagner derived the expression:

$$e.m.f. = -\frac{1}{4F} \int_{\mu'O_2}^{\mu''O_2} (tion) \, d\mu O_2 \qquad (2)$$

where,
tion—sum of ionic transference numbers of the electrolyte.
F—Faraday constant.
$\mu'O_2$—Chemical potential of oxygen at cathode.
$\mu''O_2$—Chemical potential of oxygen at anode.
for the e.m.f. produced in a galvanic oxygen concentration cell involving a mixed conduction solid electrolyte.

Wagner also explained the electric conductivity of the Nernst "glow bar" as oxygen ion conduction resulting from large concentration of mobile oxygen vacancies in the lattice. Hund who studied the density and x-ray diffractions of such mixed oxide solid electrolytes, found that a lower valent cation substituted in the lattice result in oxide vacancies providing thus a path for diffusing oxygen ions. Weininger and Zeemany were the first to demonstrate quantitatively that the oxygen ion is the carrier in solid electrolytes such as 0.85 $ZrO_2$ 0.15 $Y_2O_3$ by measuring the evolved oxygen and correlating it to the current passed through the electrolyte. Kingery and co-workers employed the stable isotope $O^{18}$ and mass spectrometer analysis to determine the oxygen ion mobility in the cubic flourite-structure phase of the solid solution 0.85 $ZrO_2$ 0.15 CaO and found it to be near unity.

Interest in oxides such as zirconia, which early in the century was directed to its possible uses as a refractory material, had shifted by the fifties to its characteristic as a solid electrolyte and workers from many countries contributed to this knowledge. This enabled workers such as Peters and Möbius to improve the design of the Haber basic gas concentration cell using mixed oxide solid electrolyte discs—$ThO_2$, $La_2O_3$, $ZrO_2$ and $Y_2O_3$ and to use it to investigate the equilibria, and at different temperatures—1000° to 1600° K. They disclose in German Democratic Republic Pat. No. 21,673 a practical design of a gas analyser based on such a cell which operates at high temperatures and uses either a gas or a scaled metal/metal oxide mixture as a reference. Ruka et al U.S. Pat. No. 3,400,054 also describe a cell construction capable of being used as a fuel cell, as an $O_2$ from gas separator or as an $O_2$ partial pressure sensor.

As operational experience was gathered from the use of such devices, many practical problems appeared and many improvements have been proposed. The most serious of these problems are:

(a) Fragility and fracture due mainly to the use of large size ceramic units with low thermal conductivity, to the presence of temperature gradients across the ceramic, and to bad thermal matching of materials, (b) large errors due to active sensor areas being within a temperature gradient, to different temperatures at the sample and reference sides, to mounting the temperature sensor at a position different from the active sensor area, and to loakage across seals, (c) errors due to sample and reference components not reaching the equilibrium temperature, (d) complex designs leading to high manufacturing cost, and difficulty in manufacturing and servicing, (e) non-versatile design leading to specialised sensors.

The present invention provides a device for monitoring a component in a fluid mixture comprising a tube, the bore of which is divided in two chambers, at a distance substantially mid-way along its length by a disc of solid electrolyte having a conducting ion corresponding to the component to be monitored, the tube being provided with heating means on either side of the disc whereby to provide the disc with even heat resulting in equal temperature on either side of the disc, and the disc being provided with electrodes on its opposed faces.

A preferred embodiment of the invention provides a device comprising a small tube having positioned across its centre a small thin solid electrolyte disc having ionic conduction appropriate to the component to be monitored. Symmetrical compartments on either side of the disc act as reference and sample chambers. A heater wire wound in grooves cut on the outside of the tube provides the disc with even heat resulting in equal temperature on either side of the disc. Metallic particles define an electronic conducting area and hold a temperature sensing element in close contact with the disc on each side. When the disc is kept at a constant temperature, and a component in a fluid of known concentration is in the reference chamber, the electrical potential across the disc is related to the concentration of the same component in the sample chamber.

The small size of the device and its symmetrical thermal design give it great resistance to thermal shock resulting in its ability to respond very quickly to changes in its required set temperature. This enables the device to be operated in a constant e.m.f. mode when a suitable reference is sealed in the reference chamber and a fixed e.m.f. operating point selected. The operating temperature is adjusted by an automatic electronic control system which alters it until the concentration of the reference component in relation to the sample component produces an output across the disc which is equal to the selected e.m.f. The temperature of the disc is then related to the concentration of the sample component.

The preferred embodiment provides a simple design which is conducive to low cost and easy manufacturing and results in a very small and rugged sensor that can survive harsh environments, large temperature fluctuations, thermal cycling and vibration, which offering at the same time a more reliable and accurate measurement.

Another feature of the design is its versatility, for example the reference and sample chambers are interchangeable and it is easily modified to have a constant flow, a static, or a sealed-in reference as desired. Also, the ease of manufacturing a disc shaped electrolyte allows a wide choice of electrolytes to suit the application.

These and other features and advantages of the present invention will become apparent from the following description of embodiments thereof when taken in conjunction with the accompanying drawings, in which.

Figure 1:
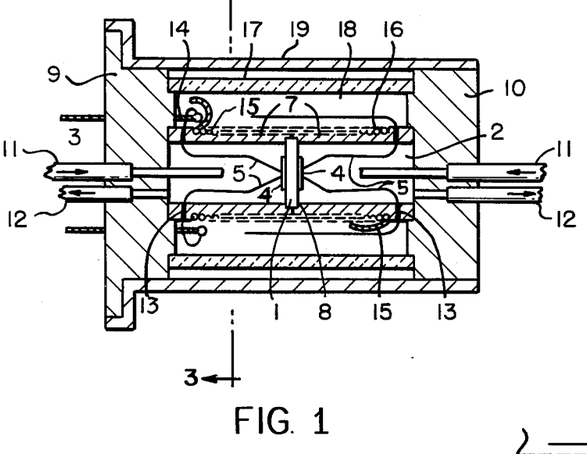
FIG. 1 shows a section through the centre of the device in its symmetrical form.

The basic construction of the device is shown in FIG. 1. A small and thin solid electrolyte disc 1, having a high ionic conductivity appropriate to the measurement required and a low electronic conductivity, separates two chambers one being a reference chamber 2 and the other a sample chamber 3 the chambers being interchangeable due to the symmetry of the design. A specific area 4 on each side of the disc is coated with a layer of porous electronically conducting powers, this can be applied by sputtering or by using a commercial paste. The choice of powder depends on whether an equilibrium state is desired, then a metal such as platinum would be suitable as the platinum acts as a catalyst to speed up the operation, or whether a nonequilibrium state is desired where a metal such as silver would be suitable.

The coating is used also to embed a thermocouple of very fine wire 5 into the centre of each face of the disc. In most cases it is found that the temperature on each face of the disc is nearly identical in which case one thermocouple suffices, and only an electrical conductor wire is needed on the opposite face. Each thermocouple provides an electronic signal related to the temperature of the associated disc face. The e.m.f. across the disc can be measured using wires of the same material from each thermocouple.

Figure 2:
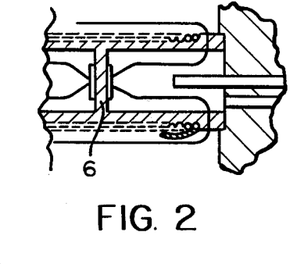
FIG. 2 shows a way of making the disc and compartments in one piece.
Figure 3:
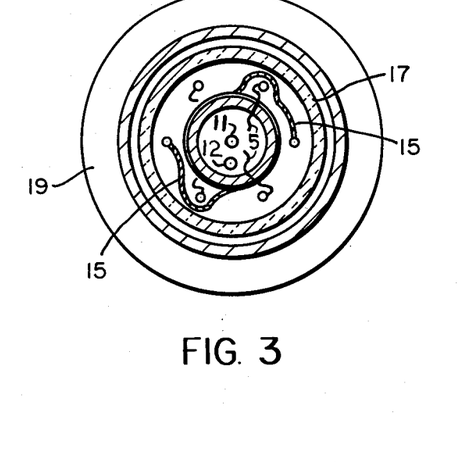
FIG. 3 shows a cross section of the device.

The chambers are defined by a thin walled ceramic cylinder manufactured out of an appropriate material having a zero porosity, this could be of the same composition as the disc or a ceramic with matching thermal characteristics. The chambers and disc can be made in one part 6, as shown in FIG. 2, if they have the same composition, or they can be made in separate cylindrical sections 7, as shown in FIG. 1. When made in sections they can be joined using a metallic based, a glass based, or a ceramic based gas tight seal 8. The end sections 9 and 10 are also joined to the chambers and sealed gas tight.

Means for admitting 11 and removing 12 a fluid to and from each chamber are provided by pipes sealed gas tight to the end sections. The choice of pipe material is dependant on the intended operating temperature range and on the degree of the corrosion potential of the fluid.

The thin electric wires 5 are brought outside the chambers, through holes 13 which are sealed gas tight, and then fused to thicker wires (14) of the same composition which provide the electrical terminations through the end section 9.

A heater wire 15 is tightly wound round the ceramic cylinder in grooves cut on its outside and covered with a ceramic cement 16. The end connections of the heater winding are also brought out through the end section 9.

A cylinder 17 of insulating material such as an appropriate ceramic is cemented with a refractory cement to the end sections 9 and the space between it and the heater can be filled with a high temperature insulation fibrous material 18. A thin stainless steel outer cover 19 cemented to the end sections 9 acts as an overall sheath.

Figure 4:
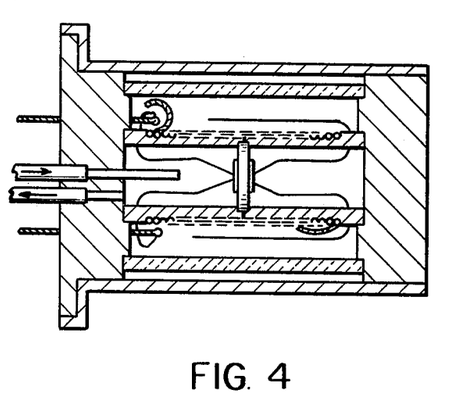
FIG. 4 shows a section through the centre of the device in its sealed-reference form.

In another embodiment, FIG. 4, the reference material is sealed in the reference compartment, thus obviating the need for the inlet and outler pipes. In yet another embodiment, FIG. 5, when the fluid to be tested is in an open environment into which the device is inserted, the fluid could diffuse into the measuring chamber through a filter disc or a flame trap 20 if necessary. The outer sheath 19 has then to be replaced by a sheath 21 opening at the trap or filter disc.

Figure 5:
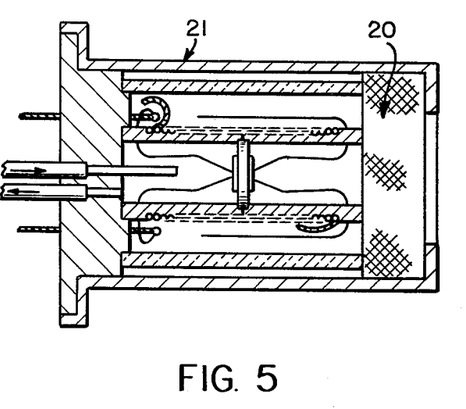
FIG. 5 shows a section through the centre of the device having a filter/flame trap form.

The reference material then could be circulated in the other chamber or sealed in as mentioned before if so desired.

Figure 6:
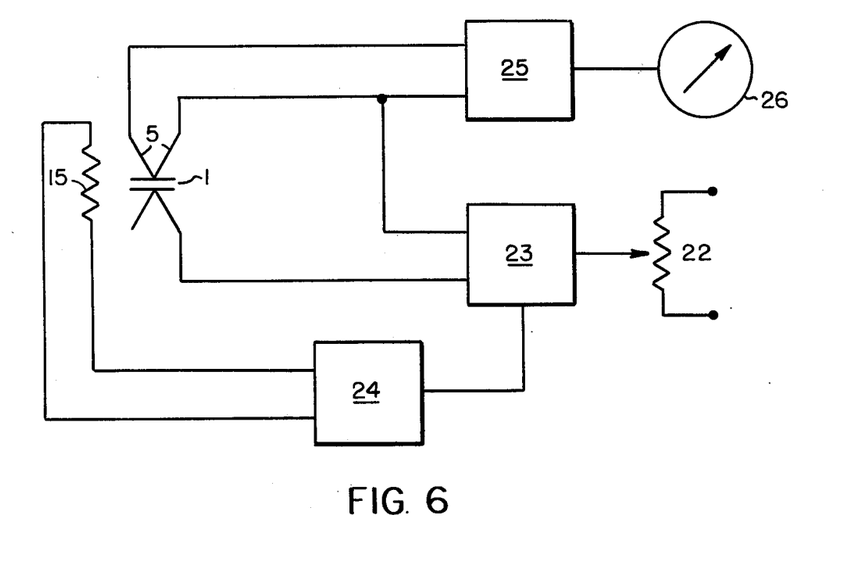
FIG. 6 shows a block diagram of the electronic control system needed to operate the device in a constant e.m.f. mode.

In operation, one possibility is that when the device has a sealed in reference, the device can be operated in a constant e.m.f. mode as outlined in the block diagram shown in FIG. 6. The desired set point or constant e.m.f. is selected from voltage divider 22. An electronic comparator 23 compares the set e.m.f. with the output voltage of the device and produces a signal, when they differ, of polarity indicating the sense of the difference which is fed to the temperature controller 24. This either increases or decreases the electrical energy reaching the heater 15, as needed to decrease the difference. The device settles down to a temperature at which the sealed-in reference produces a concentration of the component corresponding to the sample component so that the output voltage of the device is identical to the set point.

The temperature of the device is read by the thermocouple 5 and after suitable conditioning 25 can be used to drive a display 26. The most common use of these solid electrolyte device, at present is for the measurement of the partial pressure of oxygen in a gas mixture, so this application will be chosen for the following examples although by proper choice of ionic conductivity other components can be measured.

For example, if it were desired to measure chlorine, a chlorine ion conductive solid electrolyte would be chosen and a reference of metal/metal chloride would be used.

EXAMPLE 1

This is a sensor designed for measuring the oxygen partial pressure, under equilibrium conditions and using the output e.m.f. across the disc as an indication.

The design is like that shown in FIG. 5. Ambient air diffused to the chamber 2 provides the reference gas. An oxygen ion conducting material was chosen for the disc which was 4-5 mm diameter and 0.5 mm thick and had an active area of about 2 mm diameter. Pt/13% Rh 0.001 diameter wire was used for the thermocouples which were cemented using Johnson and Matthey N 758 Pt. paste. The disc was fused to the two cylindrical sections using thin copper foil and heating to over 1000° C. The heater winding was 0.002 Pt wire and was very tightly wound round the cylinder and covered with sauereisen no. 8 cement, (this was also used for all other seals, but other suitable cements may be used).

Figure 7:
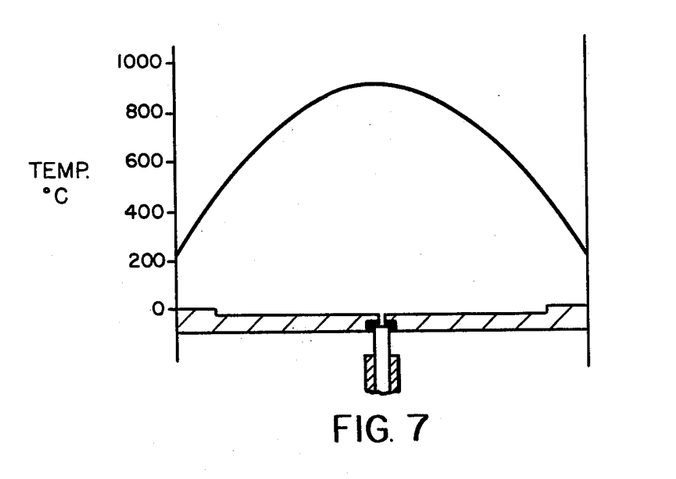
FIG. 7 shows a graph of the temperature distribution of the centre of the sensor along its length.
Figure 8:
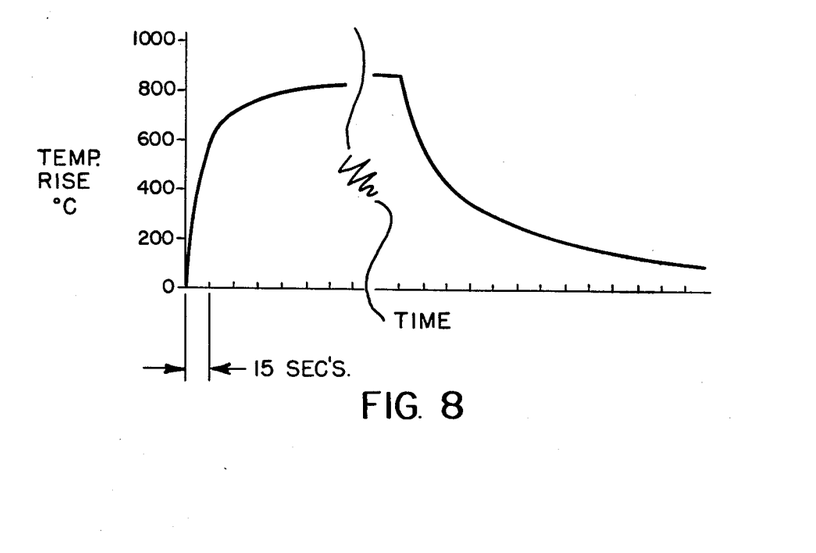
FIG. 8 shows a graph of the thermal response of the sensor to a change in set temperature.
Figure 9:
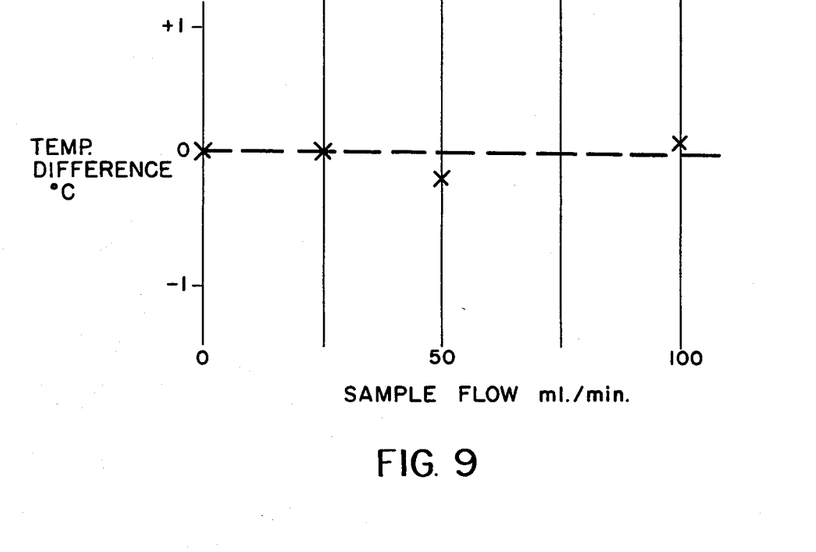
FIG. 9 shows a graph of temperature difference across the disc due to variations in sample flow rate.
Figure 10:
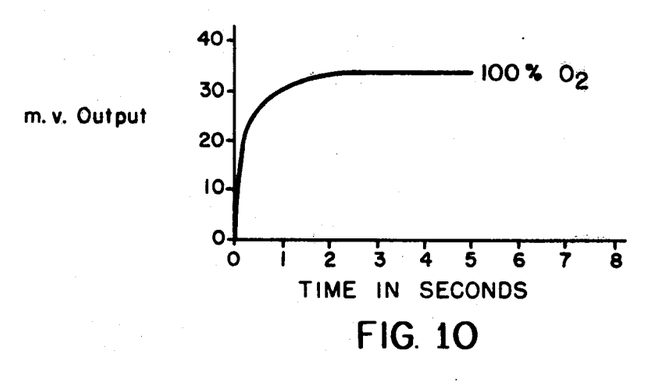
FIG. 10 shows a graph of sensor response to a step change in concentration.

The temperature distribution of the centre of the sensor along its length, with 20 W input power, is shown in FIG. 7. The measured temperature difference between the faces of the disc was less than 1° C. The response of the sensor to a change in set temperature from cold, in this case switching on 20 W, is shown in FIG. 8, where a time constant of about 15 seconds is evident. After repeated thermal cycling and shock, there was no sign of fracture in the sensor. By appropriately positioning the inlet pipe the effect of the fluid cooling the disc can be minimised as shown in FIG. 9. The response of the sensor to a step change in oxygen concentration 0-100% $O_2$ at a flow rate of 25 ml/m is shown in FIG. 10 to be about 1° C.

EXAMPLE 2

This is an example of selecting an appropriate sealed reference for oxygen measurement in the constant e.m.f. mode.

The reference is required to have an oxygen partial pressure, which is a function of temperature, that is very stable and repeatable. A system of metal/metal oxide has this feature, and the second requirement would be to find partial pressures corresponding to the range of $O_2$ measurement and in a temperature range that is within the working range of the solid electrolyte used. Thus, we can choose the range of oxygen to be within 1-100% and use one of the common oxygen type ion conductor electrolytes that operate between 800-1300 K.

Now for a metal/metal oxide system the oxygen partial pressure $C_2$ at a given temperature is given by:

$$\ln C_2 = A + BT \tag{3}$$

where A and B are constants dependant on the oxide system used.

Using this with equation (1), n=4 for oxygen.

$$e.m.f. = A + B - RT/4F \ln C_1 \tag{4}$$

Figure 11:
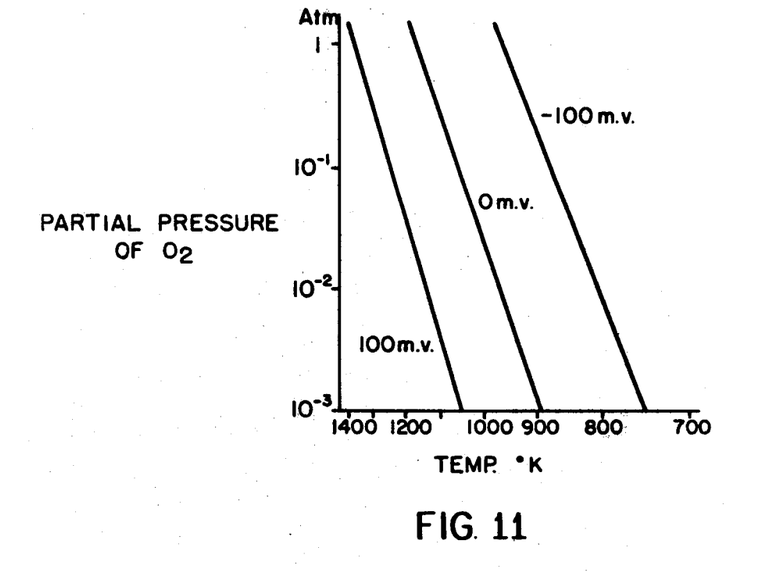
FIG. 11 shows a graph of e.m.f. v temperature for a set of constant e.m.f. lines for a Pd/PdO sealed-in reference.

An oxide system that satisfies our requirement is a Pd/Pd O system and using the data given by Fouletier in conjunction with equation (4), we can draw a family of curves each corresponding to a constant e.m.f. and relating the partial pressure of oxygen with the temperature FIG. 11. By examining this we can find a constant e.m.f. line which is suited for the oxygen range and temperature range of our sensor. Let us select the zero e.m.f. line, this gives us the partial pressure of the oxygen at the sample side $$\log C_1 = 10.3 - 11758/T \tag{5}$$

Figure 12:
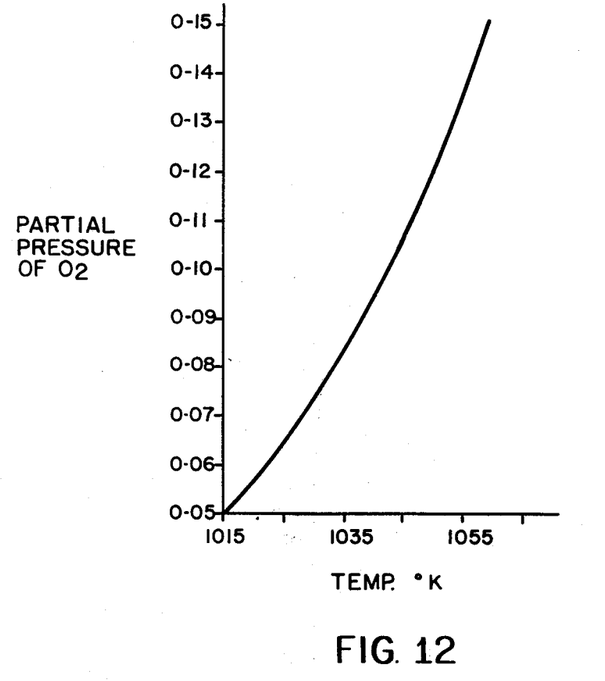
FIG. 12 shows a graph of sensor temperature for a constant e.m.f. corresponding to 10% $O_2$ set point.

This shows that the working temperature of the device is related to the sample concentration when it is operated in a constant e.m.f. mode. The variation in temperature corresponding to an oxygen sample range of 5–15% $O_2$ (total pressure—one atmosphere) for a zero e.m.f. is shown in FIG. 12.

What we claim is:

1. A device for monitoring a component in a fluid mixture comprising a solid electrolyte tube, the bore of which is divided into two chambers at a distance substantially mid-way along its length by a disc of said solid electrolyte, said tube being provided with heating means on each side of said disc; said heating means being a heat-producing element which is substantially coextensive with the length of said tube, and substantially everywhere in contact with a corresponding surface of said tube, and the periphery of said disc being continuously integral with said tube, whereby to provide said disc with even heat resulting in substantially the same temperature on each side of said disc, said disc being provided with electrodes on its opposed faces.

2. A device according to claim 1, wherein the disc and tube are integral by reason of said tube being of solid electrolyte which is the same as, and continuous with, the solid electrolyte of said disc.

3. A device according to claim 1, wherein the disc and tube are separate members which are sealed together.

4. A device according to claim 1, wherein the heating means comprises a coil of wire wound in grooves on the exterior of the tube.

5. A device for monitoring a component in a fluid mixture comprising a solid electrolyte tube, the bore of which is divided into two chambers at a distance substantially mid-way along its length by a disc of said solid electrolyte said tube being provided with heating means on each side of the disc whereby to provide the disc with even heat resulting in substantially the same temperature on each side of same disc, said disc being provided with electrodes on its opposed faces, one of said electrodes being metal particles fixed to one side of said disc, and there being a temperature sensing element held by said particles to said one side of said disc in close contact therewith.

6. A device according to any of claims 1 through 4 wherein said tube is contained within a cylinder and is everywhere spaced from the said cylinder, and there being insulation filling the space between said cylinder and said tube.

* * * * *